United States Patent [19]
Annunzio

[11] Patent Number: 5,478,236
[45] Date of Patent: Dec. 26, 1995

[54] SOLUTION DISPENSING DENTAL SYSTEM

[76] Inventor: Frank Annunzio, P.O. Box 694135, Miami, Fla. 83269

[21] Appl. No.: 178,599

[22] Filed: Jan. 7, 1994

Related U.S. Application Data

[63] Continuation of Ser. No. 796,790, Nov. 25, 1991, abandoned.

[51] Int. Cl.⁶ ..................................................... A61C 1/02
[52] U.S. Cl. ............................................. 433/98; 433/101
[58] Field of Search ...................................... 433/98, 101

[56] References Cited

U.S. PATENT DOCUMENTS

| | | | |
|---|---|---|---|
| 3,296,698 | 1/1967 | Staunt | 433/101 |
| 3,718,973 | 3/1973 | Slater et al. | 433/98 X |
| 3,732,622 | 5/1973 | Rackson | 433/101 X |
| 3,757,421 | 9/1973 | Kraft | 433/98 X |
| 3,971,375 | 7/1976 | Hill | 433/98 X |
| 4,064,630 | 12/1977 | Killick | 433/98 |
| 4,173,827 | 11/1979 | Austin, Jr. | 433/98 |
| 4,185,385 | 1/1980 | Simor | 433/101 X |
| 4,194,289 | 3/1980 | Neri | 433/101 |
| 4,201,051 | 5/1980 | Hall | 433/101 X |
| 4,286,949 | 9/1981 | Holt, Jr. | 433/101 X |
| 4,332,555 | 6/1982 | Richardson | 433/98 X |
| 4,676,750 | 6/1987 | Mason | 433/101 |
| 4,770,632 | 9/1988 | Ryder et al. | 433/98 X |
| 4,958,963 | 9/1990 | Perrault | 433/98 X |
| 5,013,240 | 5/1991 | Bailey et al. | 433/98 X |
| 5,044,952 | 9/1991 | Castellini | 433/98 X |
| 5,125,837 | 6/1992 | Warrin et al. | 433/98 |
| 5,201,899 | 4/1993 | Austin, Jr. et al. | 433/98 |
| 5,261,816 | 11/1993 | Varnes | 433/98 X |
| 5,295,829 | 3/1994 | Frey et al. | 433/98 X |

*Primary Examiner*—Nicholas D. Lucchesi
*Attorney, Agent, or Firm*—Sughrue, Mion, Zinn, Macpeak & Seas

[57] ABSTRACT

A dental solution supply system including a container for holding a solution; an air supply for supplying air; a dispensing unit, coupled to receive air supplied by the air supply, and coupled to the container, the dispensing unit operable for dispensing solution contained in the container; and a dental instrument, coupled to the dispensing unit, for receiving solution dispensed by the dispensing unit.

19 Claims, 4 Drawing Sheets

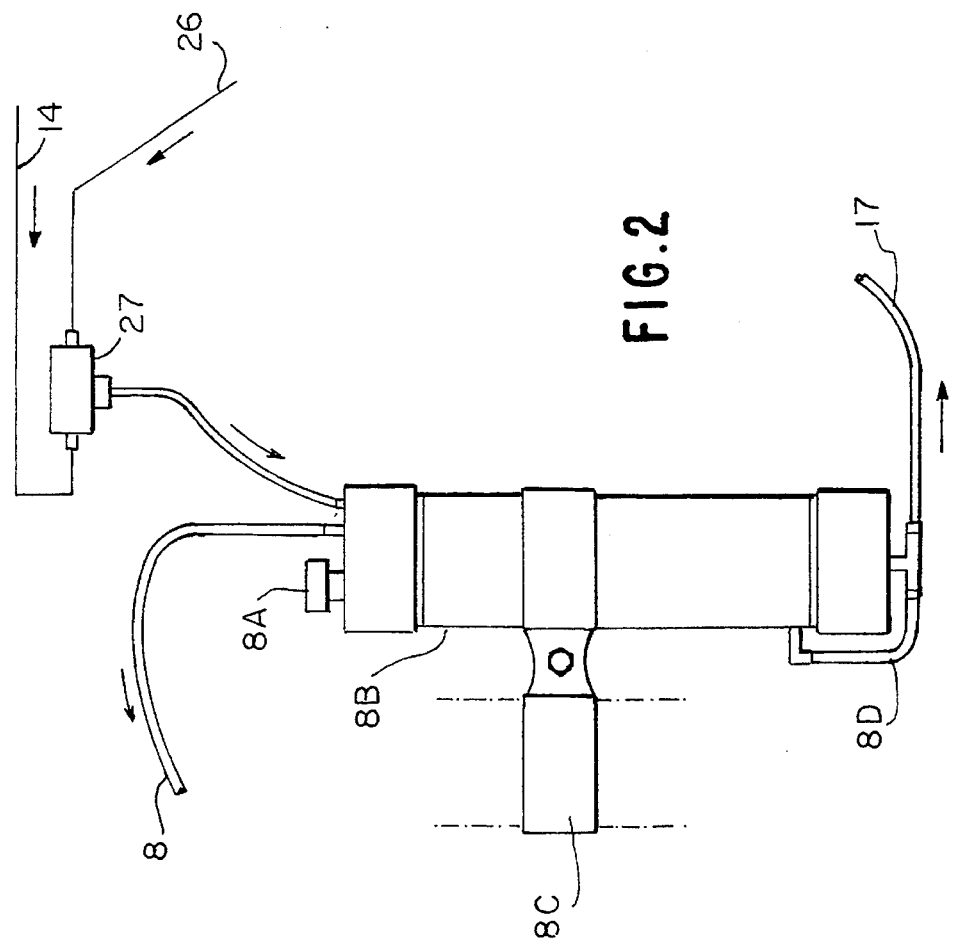
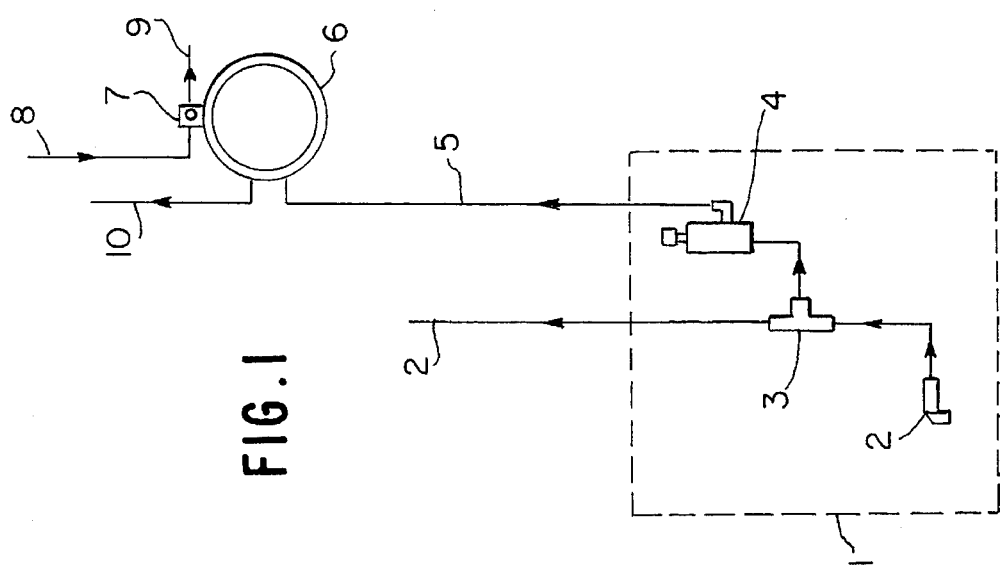

SOLUTION DISPENSING DENTAL SYSTEM

This is a Continuation of application Ser. No. 07/796,790 filed Nov. 25, 1991, now abandoned.

FIELD OF THE INVENTION

The present invention relates to a dental system for dispensing solution and, more particularly, to a dental system for dispensing solution which can be retro-fitted for use with existing dental systems.

BACKGROUND OF THE INVENTION

Most conventional dental systems include two handpieces for operating at high and low speeds, and a foot actuator for controlling the handpieces. In addition, a manual fluid spray device known as "syringe" is used during irrigation procedures. With the conventional procedure, bacteria, blood and other fluids from a patient often remain on the syringe after the patient's examination is completed. Accordingly, unless the syringe is disposed of, or proper procedures are followed to clean the syringe, such fluids may be transmitted to the next patient.

Further, the manual irrigation syringe requires the dentist or hygienist to stop and refill the manual syringes several times during an irrigation procedure, thereby increasing the time of the procedure.

The following are examples of dental systems known in the art.

U.S. Pat. No. 2,957,476 to Freeman relates to a mouth washing device including a pipe having an outlet branch and an inlet branch. According to this device a supply of medicament contained in a vessel may be introduced into the stream of liquid by opening a valve. The spray provides a cleansing and stimulating/massaging effect on the skin of the mouth and on the teeth.

U.S. Pat. No. 3,161,153 to Zorzi discloses a dental apparatus which includes an upper chamber, a lower chamber, a handle which includes valves controlled in accordance with a control lever, a first ejection pressure needle, and a second suction vacuum needle.

U.S. Pat. No. 3,718,973 to Slater et al discloses a dental system which includes three separate containers for storing various dental agents, and a foot control selector valve for regulating the supply of fluid to the system.

U.S. Pat. No. 3,949,753 to Dockhorn disclose an apparatus for supplying aseptic fluids. The apparatus includes a handpiece, a container for containing aseptic fluid, and a connecting tube for supplying air or water under pressure to a container.

U.S. Pat. No. 4,770,632 to Ryder et al discloses a delivery system for a dental treatment solution. The system includes a foot switch, a handpiece and a housing assembly in which a pumping device, a heater and a control device are located.

U.S. Pat. Nos. 4,302,185, 3,971,136, 4,865,021 and 4,470,812 are further examples of dental systems.

SUMMARY OF THE INVENTION

It is an object of the present invention to provide a retrofit irrigation system which is inexpensive, easily installed in existing dental systems, and which does not suffer from the drawbacks of the known systems.

It is another object of the invention to provide an autoclable irrigation syringe which can dispense various solutions.

These and other objects are accomplished by the dental solution supply system according to the present invention which includes:

a container for holding a solution;

air supply means for supplying air;

dispensing means, coupled to receive air supplied by said air supply means, and coupled to said container means, said dispensing means operable for dispensing solution contained in said container; and a dental instrument, coupled to said dispensing means, for receiving solution dispensed by said dispensing means.

BRIEF DESCRIPTION OF THE DRAWINGS

FIG. 1 is schematic view showing how the dental supply system according to the invention can be installed to the existing floor junction of a dental office.

FIG. 2 is a side perspective view showing the solution reservoir according to the invention.

DETAILED DESCRIPTION OF THE PREFERRED EMBODIMENT

The improved dental system according to the present invention can be easily installed in the existing floor junction of a dental office, without affecting the existing system. As shown in FIG. 1, within the existing floor junction box 1 of a dental office there is an air supply line 2. According to the invention, a tee fitting 3, an air regulator 4 and a syringe foot control 6 are installed such that the tee fitting 3, air regulator 4 and foot control 6 are coupled to the air supply line 2.

Figure 3:
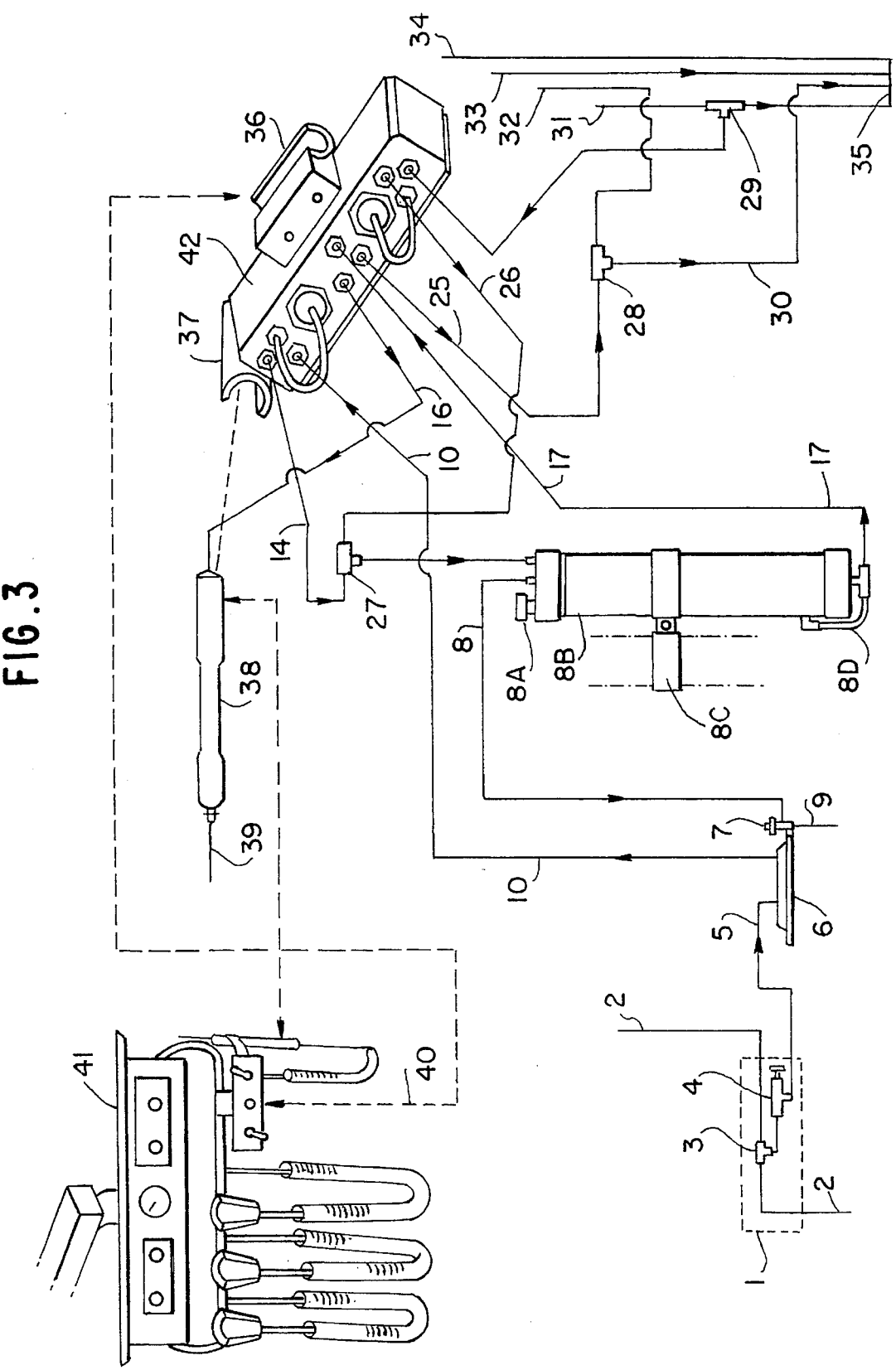
FIG. 3 is a part perspective, part schematic view showing the dental supply system according to the invention.

FIG. 3 shows the dental supply system according to the invention which includes a dental device 42. The dental device 42 includes a bracket 36 for mounting the device 42 onto the round rod of the existing dental delivery unit 41. A reservoir tank 8B, as best seen in FIG. 2, is installed to the existing light post with a connecting bracket 8C. The reservoir tank may contain medicament, mouthwash, astringent, distilled water, and other solution, as needed. Specifically, reservoir 8B may contain fluids which are used in scaling, root canal, tooth restoration, irrigation or other dental procedures. As shown in FIG. 3, a tee fitting 29 is installed onto the air drive tube 31 of a four-line handpiece tubing or onto the air drive tube of systems that use two- or three-line handpiece tubing. Shuttle valves 27 and 28 are connected to the tubing as shown in FIGS. 2–3.

Air pressure is adjusted at the regulator 4 to the recommended setting when the syringe foot control 6 is activated. The fill cap 8A of the tank 8B is removable so that the reservoir tank 8B can be filled to the proper level with solution.

Figure 5:
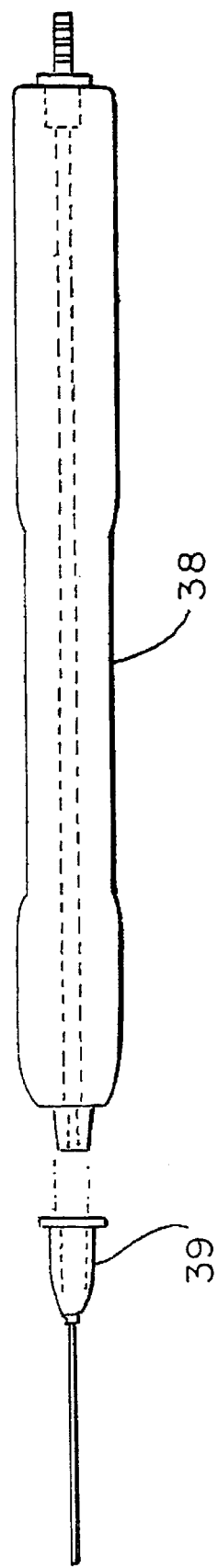
FIG. 5 is a perspective view of a syringe for use with the dental supply system according to the invention.

The operation of the irrigation syringe 38 shown in FIGS. 3 and 5 will now be described.

Figure 4:
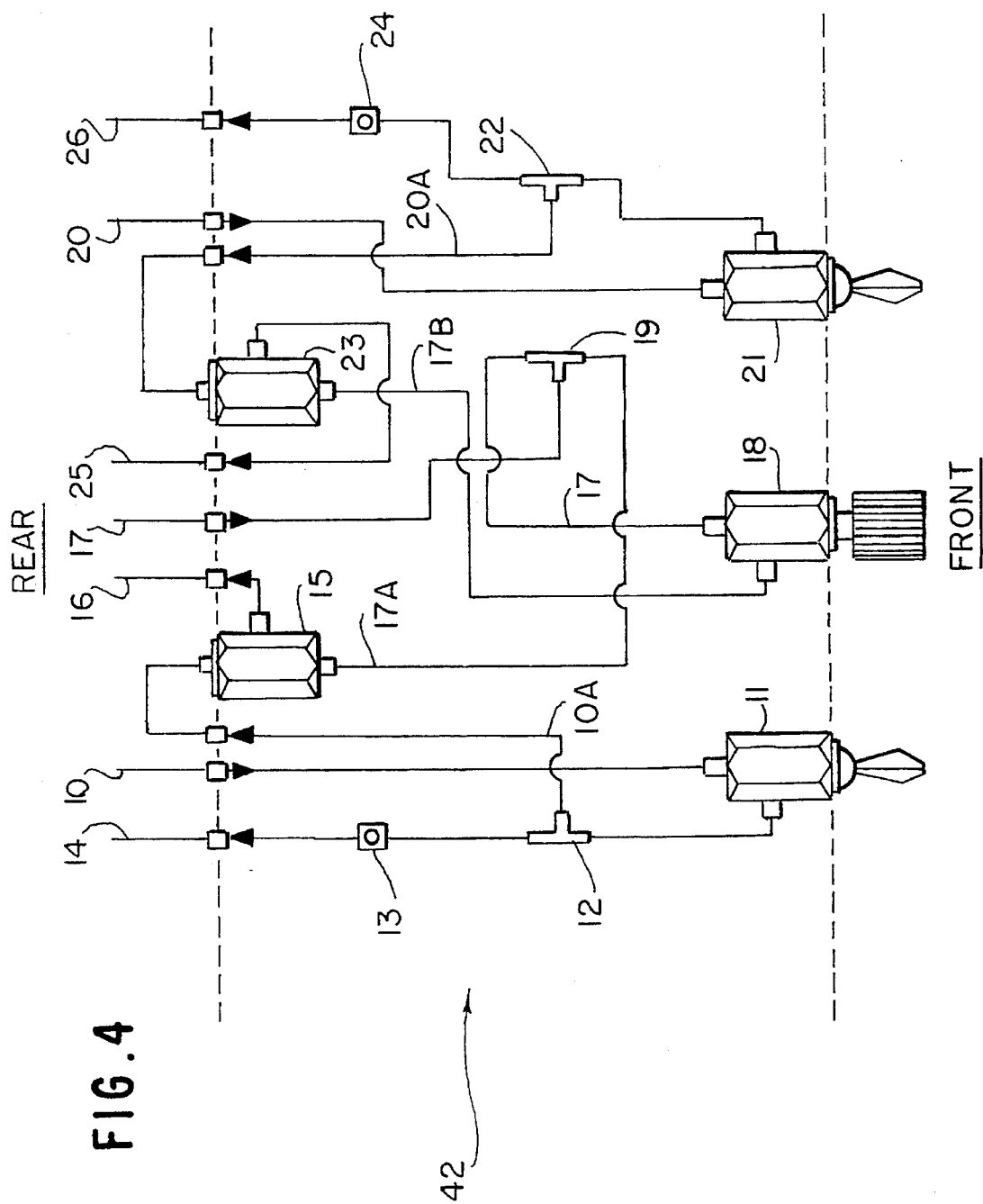
FIG. 4 is a schematic view detailing the dental supply device according to the invention.

As shown in FIG. 4, the dental supply unit 42 includes an ON-OFF valve 11 for the irrigation syringe 38. When valve 11 is switched to the ON position (i.e., the down position), and the syringe foot control 6 is activated, regulated air pressure 5 (FIG. 3) will flow from the air regulator 4 into the input side of the foot control 6. Specifically, regulated air pressure will flow from the output side of the foot control 6, as variable air pressure, into tubing 10. The regulated air pressure will then flow to the dental device 42 and will enter same at its rear via tubing 10, as shown in FIG. 4. As shown in FIG. 4, within the dental device 42 the air pressure continues through tubing 10 to the input port of the ON-OFF syringe valve 11. The air flow exits valve 11 at the output side thereof and enters a tee fitting 12. The air pressure flow will exit from two output ports of the tee fitting 12.

One output port of tee fitting 12 will flow to an air restrictor 13 and will exit same as restricted air flow through the dental device 42 via tubing 14. The other output port of tee fitting 12 will allow variable air pressure to flow to the input side of solution pilot valve 15 which contains a spring loaded piston (not shown) via tubing 10A. As the restricted air pressure flows through tubing 14, the variable air pressure in pilot valve 15 will simultaneously force the spring loaded piston which is normally in a closed position to move to the open position of the pilot valve 15. Restricted air pressure flowing through tubing 14 exits the dental device 42 to the shuttle valve 27, as shown in FIG. 3. The shuttle valve 27 only allows the restricted air to enter into the reservoir tank 8B, thereby causing the reservoir tank 8B to become pressurized. When reservoir 8B is pressurized, solution flows through tubing 17 to the dental device 42 and enters the dental device at the rear thereof (FIGS. 3 and 4). The solution continues to flow inside the device through tubing 17 and then enters a tee fitting 19. The solution will exit tee fitting 19 at two outputs.

One of the outputs of tee fitting 19 is a continuation of tubing 17 where the solution enters volume control valve 18. The solution flows from valve 18 as a controlled flow via tubing 17B to the input side of a solution pilot valve 23. The other output of tee fitting 19 flows into tubing 17A and continues to flow to the input side of solution pilot valve 15. When the syringe foot control 6 is activated, solution will exit pilot valve 15 and flow into tubing 16. Specifically, solution will then exit the dental device 42 via tubing 16 where it flows to the irrigation syringe 38 (FIGS. 3 and 5). The solution exits the irrigation syringe 38 through the disposable tip 39 mounted at a distal end thereof.

As shown in FIGS. 1 and 3, connected to the foot control 6 is a purge valve 7. The purge valve 7 is activated by foot pressure when, for example, a post drip continues at the syringe tip 39. By activating the button for the purge valve 7, air pressure in the reservoir tank 8B is released into the atmosphere via port 9 (FIG. 1), thereby stopping the post drip.

The volume flow of solution from the irrigation syringe 38 is controlled by the air pressure from the syringe foot control 6. When the selector switch on syringe valve 11 (FIG. 4) is in the off position (i.e., up position), solution will not be dispensed when the syringe foot control 6 is activated.

The operation of a dental handpiece which may be, for example, an air sonic scaler, an endomatic instrument, or a high speed dental handpiece and which can also dispense solution will now be described.

In order to operate the handpiece, the water switch on the dental delivery system 41 is switched to the OFF position, and one of the hand instruments is connected to the handpiece tubing that has been selected to dispense solution (tubing 30) or water (tubing 32). When the foot control 6 of the existing dental delivery system 41 is activated, a variable flow of air pressure will pass through the air drive tube 31 of the four-line tubing 35 as shown in FIG. 3. The variable air flow will enter a tee fitting 29 where it exits thereof at two output ports.

At one output port of fitting 29, air flow will continue to the particular hand instrument that is attached to the connector on the handpiece tubing 35. This will serve as the drive air flow for activating the particular hand instrument. The other output port of tee fitting 29 will flow to the dental device 42 via tubing 20, as shown in FIG. 3. The flow of air will enter the rear of dental device 42 via tubing 20, as best shown in FIG. 4. The flow of air will continue in the dental device via tubing 20 to the input side of an ON-OFF valve (handpiece tubing air) 21. When the ON-OFF valve 21 is in the ON position (i.e., down position), the air flow will exit valve 21 at the tee fitting 22 at two output ports thereof.

At one output port of tee fitting 22 variable air pressure enters tubing 20A and flows to the input port of solution pilot valve 23 (for handpiece tubing), as shown in FIG. 4. The other output port of tee fitting 22 flows into the restrictor 24 and exits thereof as restricted air flow in tubing 26. The restricted air flow will exit the dental device via tubing 26 to one input port of shuttle valve 27, as shown in FIG. 3. The shuttle valve 27 allows the restricted air only to exit into the reservoir tank 8B, thereby causing the reservoir tank to become pressurized. As a result of the reservoir tank 8B becoming pressurized, solution within the tank is forced out into tubing 17 where it flows to the dental device 42 and enters the dental device at the rear thereof, as best shown in FIG. 4. The solution continues to flow via tubing 17 within the dental device to tee fitting 19 where the solution exits tee fitting 19 from two output ports.

One of the output ports is a continuation of tubing 17 where solution flows to the input side of solution volume valve 18. The solution flows via the volume valve 18 to the solution pilot valve 23 via tubing 17B. The solution exits valve 23 and flows in tubing 25 where it exits the dental device 42 at the rear thereof. As shown in FIG. 3, the controlled solution flows via tubing 25 to the shuttle valve 28. The solution exits the shuttle valve 28 via tubing 30 and continues to flow to and out of the particular hand instrument connected to tubing 35. The other output port of the fitting 19 (FIG. 4) allows flow via tubing 17A to solution pilot valve 15 and to the irrigation syringe 38 via tubing 16.

The dental delivery system 41 will dispense solution when the water ON-OFF switch of the system is in the off position, and the ON-OFF valve 21 on the dental device 42 is in the ON position. By pressing the existing dental delivery foot control, solution will be dispensed through one of the hand instruments of the dental device 42. The volume control valve 18 on the dental device will control the volume of flow to the instrument.

When water rather than solution is required, the water ON-OFF switch of the system is switched to the on position and the ON-OFF valve 21 switched to the off position. By pressing the foot control, water will be dispensed through one of the hand instruments.

What I claim is:

1. In a dental station of the type having a stationary junction box which includes an air supply line, a dental unit connected to receive air from the air supply line and having a selection unit for selectively providing air from the air supply line, and a plurality of dental handpieces of the type used for cleaning and drilling teeth, the plurality of dental handpieces being connected to the dental unit so as to selectively receive air from the air supply line, the improvement comprising:

a delivery unit connected to receive air from the air supply line and for selectively providing air from the air supply line;

a container for containing a fluid, said container being connected to receive air selectively provided from said delivery unit, said delivery unit being connected to receive fluid contained in said container, and said container being separate from said delivery unit; and a dental irrigation syringe connected to said delivery unit for receiving the fluid provided to said delivery unit from said container.

2. The dental station as defined in claim 1, wherein the fluid contained in said container is an irrigating medicament.

3. The dental station as defined in claim 1, wherein the fluid contained in said container is one of medicament, mouthwash, astringent and distilled water.

4. The dental station as defined in claim 1, further comprising a foot pedal connected to the air supply line and to said delivery unit for selectively allowing air to be supplied to said delivery unit.

5. The dental station as defined in claim 4, wherein said foot pedal includes a purge valve and a port.

6. The dental station as defined in claim 5, further comprising tubing for connecting said container to said port of said foot pedal such that activation of said purge valve causes air pressure in said container to be released through said port.

7. The dental station as defined in claim 1, further comprising tubing for connecting said container to said delivery unit such that said delivery unit is operable for supplying air to said container to pressurize said container, thereby causing the fluid container in said container to be provided to said delivery unit.

8. The dental station as defined in claim 7, wherein said delivery unit includes a switch for selectively controlling whether fluid provided from said container is received by said delivery unit.

9. The dental station as defined in claim 1, wherein said container is separate and spaced from said irrigation syringe.

10. The dental station as defined in claim 1, wherein said irrigation syringe includes a disposable tip mounted at a distal end thereof.

11. The dental station as defined in claim 1, wherein said delivery unit is mechanically coupled to the dental unit.

12. The dental station as defined in claim 11, wherein the dental station includes a rod, and wherein said delivery unit includes a bracket which is mounted to the rod of said dental station.

13. The dental station as defined in claim 12, wherein said container includes a connecting bracket for connecting to a post.

14. The dental station as defined in claim 1, wherein the said container includes a connecting bracket for connecting to a post.

15. In a dental station of the type having a stationary junction box which includes an air supply line, a dental unit connected to receive air from the air supply line and having a selection unit for selectively providing air from the air supply line, and a plurality of dental handpieces of the type used for cleaning and drilling teeth, the plurality of dental handpieces being connected to the dental unit so as to selectively receive air from the air supply line, the improvement comprising:

a delivery unit connected to receive air from the air supply line and for selectively providing air from the air supply line;

a container for containing an irrigating medicament, said container being connected to receive air selectively provided from said delivery unit and said container being separate from said delivery unit and said container being separate from said delivery unit; and a dental irrigation syringe connected so as to receive the irrigating medicament contained in said container, wherein said delivery unit is mechanically coupled to the dental unit of the dental station.

16. The dental station as defined in claim 15, wherein said container is separate and spaced from said irrigation syringe.

17. The dental station as defined in claim 15, wherein said irrigation syringe includes a disposable tip mounted at a distal end thereof.

18. The dental station as defined in claim 15, wherein said container includes a connecting bracket for connecting to a post.

19. The dental station as defined in claim 15, wherein the dental unit includes a rod, and said delivery unit includes a mounting bracket which is mounted to the rod of said dental unit.

* * * * *

UNITED STATES PATENT AND TRADEMARK OFFICE
CERTIFICATE OF CORRECTION

PATENT NO.   : 5,478,236
DATED        : December 26, 1995
INVENTOR(S)  : Annunzio It is certified that error appears in the above-indentified patent and that said Letters Patent is hereby corrected as shown below:

On the title page, left column, item [76], delete "P.O. Box 694135, Miami, Fla. 83269" and insert: --6221 Southwest 32nd Street, Miramar, Fla. 33023--.

Signed and Sealed this

Twenty-eighth Day of May, 1996

Attest:

BRUCE LEHMAN

*Attesting Officer*         *Commissioner of Patents and Trademarks*